(12) United States Patent
Bastia

(10) Patent No.: US 8,512,237 B2
(45) Date of Patent: Aug. 20, 2013

(54) MEDICAL DEVICE FOR COLO-PROCTOLOGICAL PATHOLOGIES

(75) Inventor: Filippo Bastia, Carpi (IT)

(73) Assignee: THD S.p.A., Correggio (IT)

( * ) Notice: Subject to any disclaimer, the term of this patent is extended or adjusted under 35 U.S.C. 154(b) by 0 days.

(21) Appl. No.: 13/181,881

(22) Filed: Jul. 13, 2011

(65) Prior Publication Data

US 2012/0016204 A1 Jan. 19, 2012

(30) Foreign Application Priority Data

Jul. 15, 2010 (IT) ............................. RE2010A0059

(51) Int. Cl.
*A61B 1/32* (2006.01)

(52) U.S. Cl.
USPC ........................... 600/245; 600/212; 600/249

(58) Field of Classification Search
USPC ................. 600/205, 208, 212, 223, 245, 246, 600/248, 249
See application file for complete search history.

(56) References Cited

U.S. PATENT DOCUMENTS

| | | | |
|---|---|---|---|
| 2,482,971 A | 9/1949 | Golson | |
| 3,532,088 A | 10/1970 | Fiore | |
| 3,870,036 A * | 3/1975 | Fiore | 600/184 |
| 6,004,265 A * | 12/1999 | Hsu et al. | 600/223 |
| 6,379,296 B1* | 4/2002 | Baggett | 600/178 |
| 6,616,603 B1* | 9/2003 | Fontana | 600/199 |
| 2003/0163026 A1 | 8/2003 | Fontana | |
| 2009/0259110 A1 | 10/2009 | Bastia et al. | |
| 2009/0306481 A1* | 12/2009 | Bastia | 600/249 |
| 2011/0130771 A1 | 6/2011 | Bastia et al. | |

FOREIGN PATENT DOCUMENTS

| | | |
|---|---|---|
| EP | 1183991 A2 | 3/2002 |
| WO | 2007094016 A1 | 8/2007 |
| WO | WO 2007094016 A1 * | 8/2007 |

* cited by examiner

*Primary Examiner* — Eduardo C Robert
*Assistant Examiner* — Julianna N Harvey
(74) *Attorney, Agent, or Firm* — Pearne & Gordon LLP

(57) ABSTRACT

A medical device 1 for colo-proctological pathologies, comprising a retractor body 2, having a distal end 3 and a proximal end 4, a handle 7 connected to the retractor body 2, and illuminating means 16, located internally of a cavity 12 fashioned internally of the proximal end 4, for generating a light beam internally of the retractor body 2.

13 Claims, 4 Drawing Sheets

MEDICAL DEVICE FOR COLO-PROCTOLOGICAL PATHOLOGIES

FIELD OF THE INVENTION

The present invention relates to a medical device for colo-proctological pathologies.

Said device has a field of application in the medical realm, both for the diagnosis of colo-proctological pathologies and for the treatment thereof with ambulatory and non-ambulatory surgical intervention.

BACKGROUND OF THE INVENTION

The term colo-proctological pathologies means all disorders that directly or indirectly affect the recto-intestinal tract of the human body, such as, for example, haemorrhoids, anal rhagades, internal mucosal prolapses, anal fistulas, rectovaginal fistulas, condylomata, rectoceles, anal cancer, polyps, anal fibrosis, hypertrophic anal papillae, rectal prolapse, ulcerative rectocolitis, polyposis, colorectal tumours and/or the like.

Various devices for aiding in the detection or treatment of the above-mentioned pathologies are known in the medical field, some of which have in common the presence of a retractor body with a handle, the retractor body being insertable in the anal cavity and associated with a light source capable of illuminating the inside of the retractor body when the latter is inserted.

The retractor body aids in dilating the side walls of the anal canal, which are contractile as they consist of muscular tissue, and the light source aids visibility inside the anal canal, which would otherwise be dark, so that the physician can perform a diagnosis or surgically operate.

In the prior art there exist various implementational solutions for transmitting light, by means of a light source, internally of the retractor body.

Among them, devices are known wherein the handle of the retractor body is removably connected to a light source.

The light emitted by the light source is then directed against a curved optical fibre, or body of transparent material defined in the art as a "light guide body", which tends to direct the light internally of the retractor body.

The prior art solution presents several disadvantages.

In the case of a light source powered by means of an electric cable, the latter makes movement of the retractor body, specifically, rotation of the retractor body, inside the anal canal difficult, penalizing the instrument's manoeuverability.

To remedy this problem the light source is powered by means of a battery housed inside the handle.

Another disadvantage tied to the illuminating devices known in the art, irrespective of whether they are powered with an electric cable or battery, is the quantity of light dispersed by the light source in the retractor body.

In fact, the power radiated by the light source being equal, the optical fibre, or transparent light guide body, causes a dispersion of the light transmitted internally of the retractor body.

The dispersion is due to the interposition, between the light source and inside of the retractor body, of a further means which in any case absorbs part of the light radiated by the source.

Secondly, the curved shape of the optical fibre, or light guide body, necessary to direct the light beam into the retractor body, which has a horizontal axis, from the handle, whose axis is oblique relative to that of the retractor body, does not permit a complete deviation of the light inside the retractor body.

Moreover, a further disadvantage of these devices lies in the possibility that organic fluid may cover a portion of the optical fibre, or light guide body, thus reducing the power radiated by the light source internally of the retractor body.

SUMMARY OF THE INVENTION

The object of the present invention is to produce a medical-surgical device for colo-proctological pathologies which is able to optimize the radiating power emitted by the light source internally of the retractor body.

The specified object, and still others, are substantially achieved by a medical-surgical device for colo-proctological pathologies as set forth in the appended claims.

BRIEF DESCRIPTION OF THE DRAWINGS

A description will now be provided, by way of example, of a non-exclusive embodiment of a medical-surgical device for colo-proctological pathologies in accordance with the appended figures, in which.

DETAILED DESCRIPTION OF THE INVENTION

Figure 1:
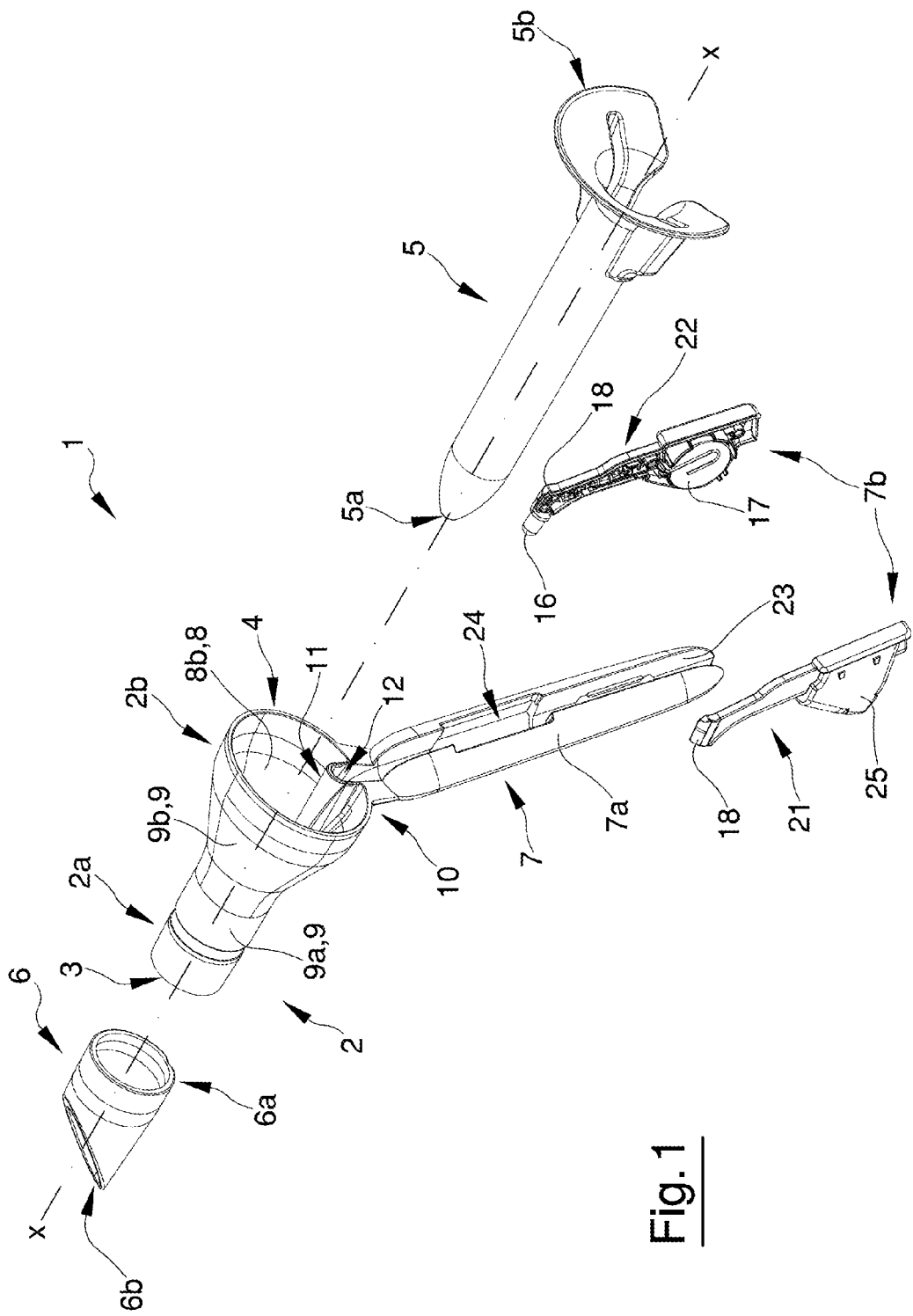
FIG. 1 illustrates an exploded axonometric view of a medical device for colo-proctological pathologies according to the present invention.

With reference to the appended figures, 1 indicates in its entirety a medical device for colo-proctological pathologies according to the invention.

Said device 1 is defined in the upper part by a retractor body 2.

Said retractor body 2 has a substantially tubular conformation.

Said retractor body 2 has a direction of development along a prevalent X-X axis.

Said prevalent X-X axis of development is preferably horizontal.

As can be seen in FIGS. 1-4, the retractor body 2 exhibits a distal end 3 and a proximal end 4.

The distal end 3, having a circular cross section, is open and insertable in the anal cavity by means of an introducer body 5.

Said introducer body 5, having a direction of development coinciding with the X-X axis of the retractor body 2, is defined by a tubular body having at one end a pointed portion 5a, suitable for aiding the insertion of the introducer body 5 and consequently of the retractor body 2 into the anal cavity, and at the opposite end a flared portion 5b, suitable for aiding better visibility internally of the retractor body 2.

Said introducer body 5 is removably and slidably insertable into the retractor body 2.

During use, the surgeon inserts the introducer body 5 into the retractor body 2, causing the former to slide inside the latter, until the tapered portion 5b comes up against the proximal end 4 of the retractor body 2. Following insertion of the introducer body 5, and consequently of the retractor body 2, the surgeon extracts the introducer body 5 from the retractor body 2, thus having full access to the anal cavity through the distal end 3 of the retractor body 2.

At the distal end 3 an extension 6 is present.

The extension 6 has a first end 6a, coupled to the distal end 3, and a second end 6b.

The aforesaid extension 6 also has a direction of development coinciding with the prevalent X-X axis of the retractor body 2.

The first end 6a has a circular cross section whereas the second end 6b has an elliptical cross section.

With reference to the prevalent X-X axis, the cross section of the first end 6a is generated by a plane perpendicular to the X-X axis whereas the cross section of the second end 6b is generated by a plane oblique to the aforesaid axis.

It is understood that, without going outside the scope of protection of the present invention, the extension 6 can take on any other form or be produced in one piece with the retractor body 2.

The proximal end 4 is also open and has a circular cross section.

Figure 2:
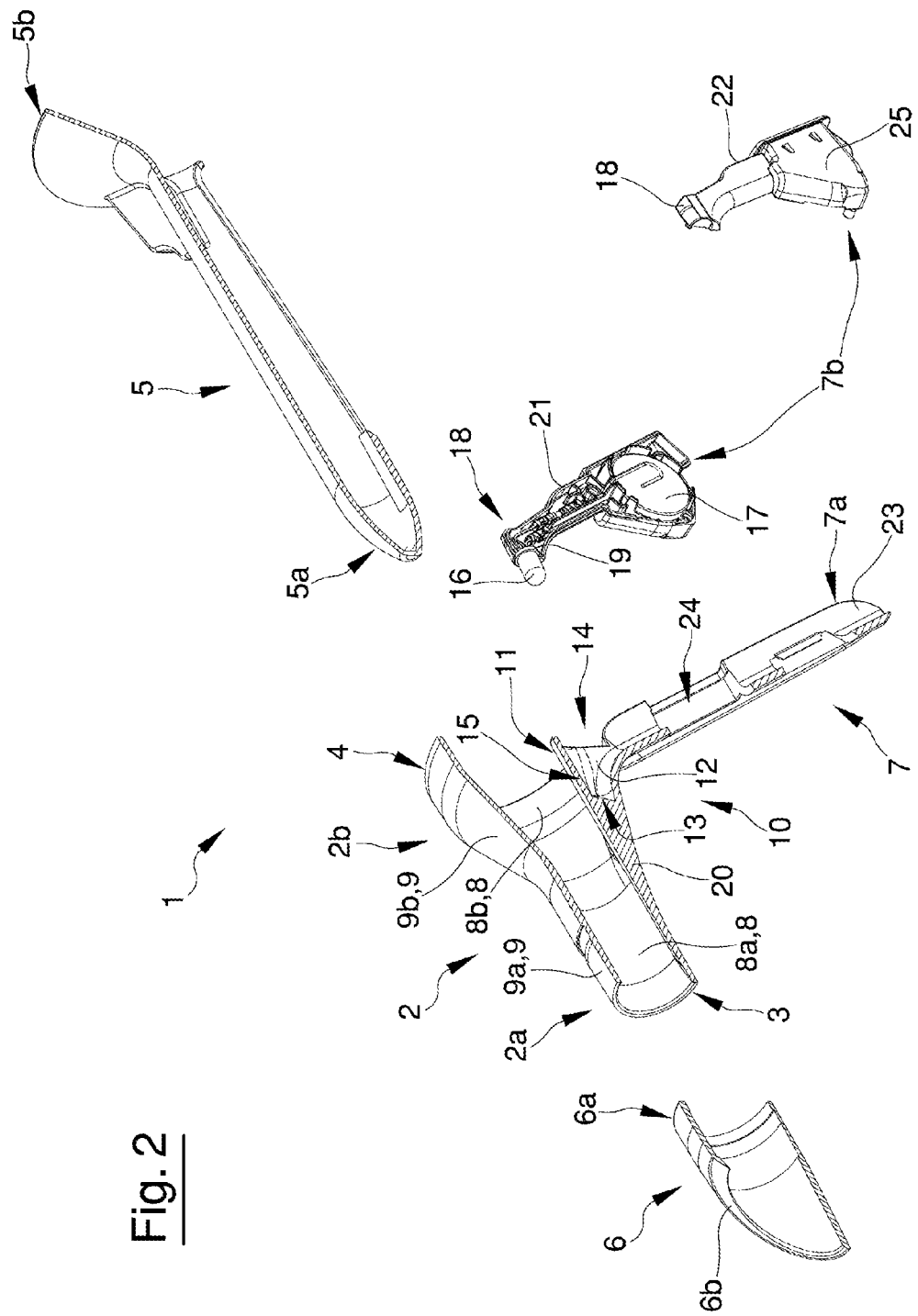
FIG. 2 illustrates a sectional exploded axonometric view of the device of FIG. 1.

As can be better seen from FIGS. 1 and 2, the retractor body 2 is defined by a first section 2a and a second section 2b.

The first section 2a starts from the distal end 3 and extends away from it toward the proximal end 4.

Said first section 2a has a substantially tubular shape.

The second section 2b extends from approximately the centre line of the retractor body 2, downstream of the first section 2a.

Said second section 2b has a substantially truncated cone shape.

The second section 2b continues the first section 2a until terminating with the proximal end 4.

Consequently, the retractor body 2 extends along its prevalent X-X axis of development, from the distal end 3 with a first section 2a and continues with a second section 2b until terminating with the proximal end 4.

In other words, the retractor body extends along its prevalent X-X axis of development, from the distal end 3 with a cylindrical section, defined by the first section 2a, and continues with a truncated cone section, with a broadening of the cross section defined by the second section 2b, terminating with the proximal end 4.

Extending from the second section 2b, at the proximal end 4, there is a handle 7.

Said handle 7 is connected to the retractor body 2 in a connecting portion 10 located downstream of the second section 2b at the proximal end 4.

Said handle 7 is defined by a first element 7a, solidly constrained to the retractor body 2 in the connecting portion 10, and a second element 7b removably coupled to the first element 7a.

The retractor body 2 exhibits a first internal surface 8 and a second external surface 9.

The first internal surface 8 confines internally thereof a volume for inspection and/or for operating in the anal cavity.

The second external surface 9 is at least in part in contact with the anal cavity when the retractor body 2 is inserted therein.

The first internal surface 8 is defined by a first cylindrical section 8a, extending for the first section 2a of the retractor body, and a first truncated cone-shaped section 8b, extending for the second section 2b of the retractor body 2.

The second external surface 9, analogously to the first internal surface 8, is defined by a second cylindrical section 9a, extending for the first section 2a of the retractor body, and by a second truncated cone-shaped section 9b, extending for the second section 2b of the retractor body 2.

At the connecting portion 10, between the handle 7 and proximal end 4, a protuberance 11 is present inside the retractor body 2.

Said protuberance 11, located at the proximal end 4 of the retractor body, is defined by an extension of the first internal surface 8 away from the second external surface 9 of the retractor body.

Said protuberance 11 defines a thickening of material 20 between the internal surface 8 and the external surface 9.

A cavity 12 is afforded internally of the protuberance 11.

Said cavity 12 interrupts the thickening of material 20, extending from the proximal end 4 at least in part into the thickening of material 20.

Said cavity 12 is located at the proximal end 4.

The cavity 12 is defined, internally of the retractor body 2, by a front side 13, a rear side 14 and a laterally-developing wall 15 conjoining the front side 13 to the rear side 14.

The front side 13 and the laterally-developing wall 15 are entirely contained internally of the retractor body 2.

The rear side 14 is open, communicating with the outside of the retractor body 2 at the proximal end 4.

The surgical device 1 further comprises illuminating means or illuminator 16 for generating a light beam L directed from the proximal end 4 towards the distal end 3.

Said illuminating means 16 are preferably defined by a LED light.

Said illuminating means 16 are contained internally of the cavity 12.

The application of illuminating means 16 directly inside the retractor body 2, at their own cavity 12, makes it possible to avoid adopting light guide bodies or optical fibres, or means suitable for converging a light beam and not for training it.

Figure 3:
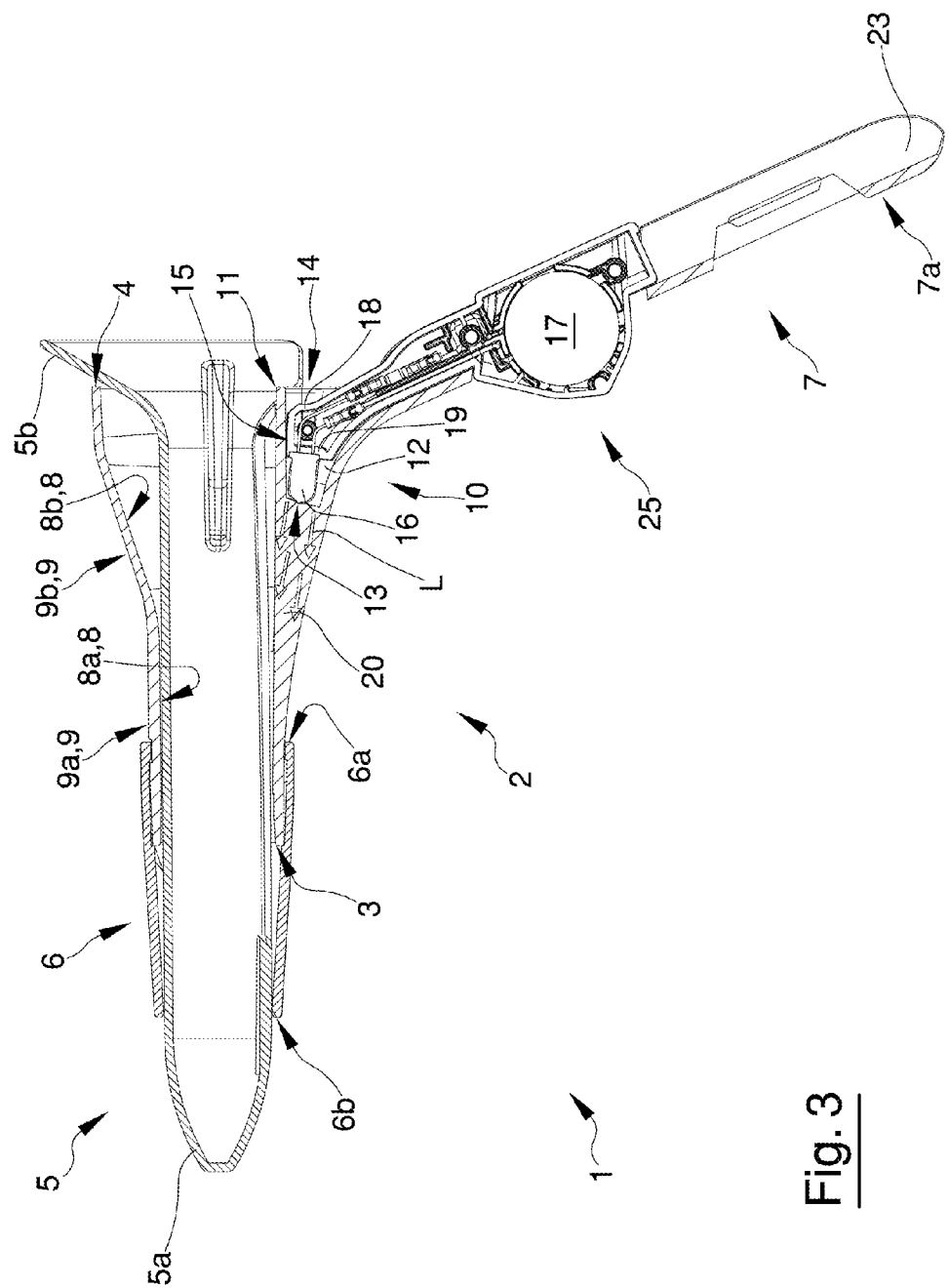
FIG. 3 illustrates a side sectional view of the device of FIG. 1 in an assembled configuration.

As can be seen in FIG. 3, the illuminating means 16 are entirely contained internally of the cavity 12 so as to train the light beam L against the front closed side 10 of the cavity 12.

In other words, the illuminating means 16 train a light beam L, which develops internally of the protuberance 11, becoming channelled against the thickening of material 20, or between said first internal surface 8 and said second external surface 9 of the retractor body 2.

As can be seen in FIG. 3 the protuberance 11 is the seat housing the cavity 12 and hence the illuminating means 16.

Said illuminating means 16 are powered by a power source 17.

The power source 17, preferably defined by a button battery, is entirely contained internally of the manoeuvering handle 7, the latter being located at the lower part of the surgical device.

As previously noted, the handle 7 is defined by a first element 7a and a second element 7b.

Said second element 7b is in turn defined by a first half-shell 21 and a second half-shell 22.

With particular reference to the first element 7a, the latter comprises a second seating 23, extending for the whole extent of the first element 7a, so as to house the second element 7b.

Said second seating 23 is interrupted by a window 24 suitable for receiving a corresponding protuberance 25, solidly constrained to the second element 7b, so as to favour the connection and coupling stability between the first and second elements 7a, 7b.

With particular reference to the second element 7b, the latter comprises a termination 18 serving to close the rear open side 14 of the cavity 12.

Said illuminating means 16 are located internally of the cavity 12 by means of the second element 7b.

In fact, said second element 7b comprises a termination 18 having a first seating 19 for housing the light source.

The first annular seating 19 retains the illuminating means 16 in such a way as to enable the light beam L to be directed against the front closed side 13 of the cavity 12.

Said termination 18 moreover aids the closure of the cavity 12.

In this manner it is possible to prevent organic fluid or another obscuring material from being able to enter the cavity 12 during use of the surgical device 1 and cover the illuminating means 16, thus weakening the light beam L passing through the retractor body 2.

Below the termination 18, the first and second half-shell 21, 22 define the protuberance 25 suitable for being inserted inside the window 24 of the first element 7a and extending beyond the latter.

With this configuration said protuberance 25, constituting a valid rest for the surgeon's hand, optimizes the gripping ergonomics of the handle 7.

Said protuberance 25 moreover fulfils the further function of a shell for housing and containing the power source 17 of the illuminating means 16.

Figure 4:
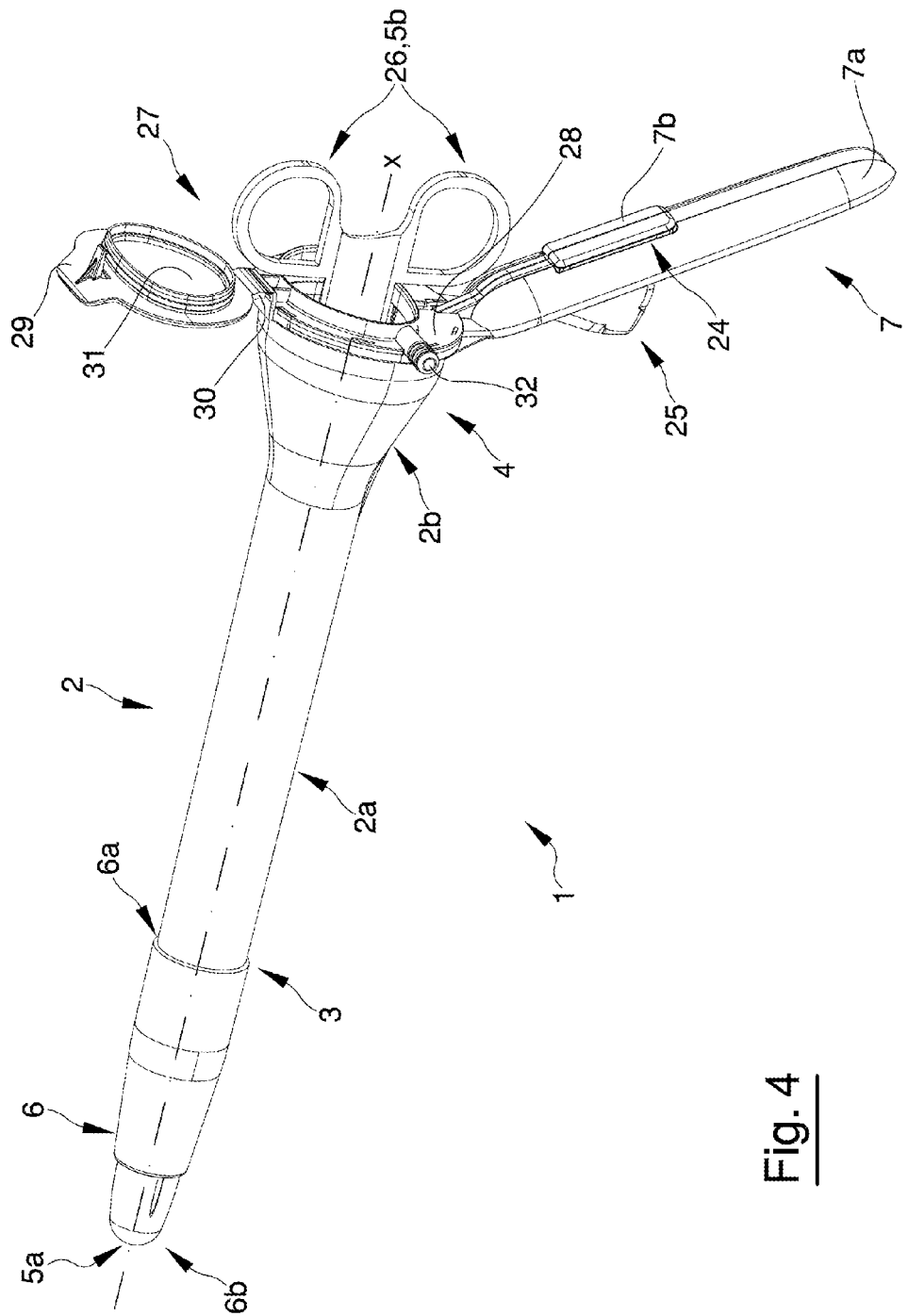
FIG. 4 illustrates an axonometric view of a second embodiment of the medical device for colo-proctological pathologies according to the present invention.

With reference to the device 1 of FIG. 4, it may be noted that the same exhibits a conformation analogous to that of the device of FIGS. 1-3.

The latter device, mainly adopted to perform ambulatory examinations, differs in the greater extension of the retractor body 2 along the direction of development X-X.

With reference to the proximal end 4 of the device, in FIG. 4 it is possible to note that the introducer body 5 terminates with gripper means 26 in place of the tapered portion 5b.

Said gripper means 26 facilitate the insertion and extraction of the introducer body 5 from the retractor body 2 in virtue of the greater extension thereof along the X-X axis.

Coupled to the proximal end 4 of the retractor body 2 there is a cover 27 for favouring a hermetic seal of the inside of the retractor body 2.

Said cover 27 is defined by a base 28, coupled to the proximal end 4, and by a flip-up portion 29 which is movable relative to the base 28 by means of a hinge coupling 30.

On the inside of the flip-up portion 29 a lens 31 is afforded to favour a better visibility, given by a magnification of the operating area, internally of the retractor body 2.

At the base 28 there is a cannula 32 suitable for aiding, when the cover 27 is closed, a communication of air from outside the retractor body 2 into the latter.

Through the cannula 28 the surgeon, upon inserting the retractor body 2 into the anal cavity, can promote the introduction of air into the anal cavity.

In this manner, should the insertion of the retractor body 2 meet resistance to insertion of the device due to anal contractions of the patient, the surgeon can dilate the anal walls by introducing air into the cannula 32, and hence into the retractor body, thus favouring the dilatation of the anal canal and the consequent insertion of the retractor body 2.

The above-described medical device for colo-proctological pathologies 1 achieves numerous important advantages.

First of all, the power emitted by the illuminating means 16 being equal, the light emitted by the latter inside the retractor body 2 allows better visibility internally thereof.

That is in virtue of the fact that between the illuminating means 16 and retractor body 2 any further means of transmitting light inside the retractor body have been eliminated.

Providing a cavity 12 inside the retractor body 2 allows the light beam L to be transmitted internally thereof directly and without interposition of other means.

In addition, the positioning of the illuminating means 16 directly inside the retractor body 2 does not bring about any deviation of the light outside the precise operating area, a factor which manifested itself with the use of light guide bodies that were curved or had oblique axes relative to the prevalent axis of development of the retractor body.

Such optimization of the radiating power inside the retractor body makes it possible to adopt less powerful batteries and thus to economize the cost of producing the device 1.

The protection of the illuminating means 16 inside the cavity 12 moreover prevents episodes of obscuration of the aforesaid means or of the light transmitting means which in prior art devices manifested themselves each time organic fluid, faeces or other substances came into contact with and/or near the light guide body.

The invention claimed is:

1. A medical-surgical device for colo-proctological pathologies, comprising
a one-piece retractor body which has been integrally provided as a single piece, the retractor body (a) having a direction of development along a prevalent axis, (b) having a distal end insertable in an anal cavity, and (c) having a proximal end, the retractor body having a side wall connecting the distal end to the proximal end;
a handle, connected to the retractor body adjacent the proximal end for facilitating manoeuverability of the retractor body internally of the anal cavity;
an illuminator for generating a light beam directed from the proximal end towards the distal end;
wherein the one-piece retractor body comprises a cavity afforded internally thereof in the side wall, the cavity extending from the proximal end of the one-piece retractor body towards the distal end of the one-piece retractor body, and wherein the illuminator is entirely contained internally of the cavity for generating the light beam directly internally of the retractor body, the cavity having a closed front side and an open rear side, the cavity being enclosed by a top, laterally-developing walls and a bottom, the open rear side being uncovered.

2. The device of claim 1, characterised in that the retractor body exhibits a first internal surface, confining internally thereof a volume for inspection or for operating in the anal cavity, and a second external surface in contact with the anal cavity when the retractor body is inserted therein.

3. The device of claim 2, characterised in that the cavity is entirely contained between the internal surface and the external surface of the retractor body.

4. The device of claim 2, characterised in that the internal surface exhibits, at the proximal end of the retractor body, a protuberance.

5. The device of claim 4, characterised in that the cavity is afforded internally of the protuberance.

6. The device of claim 4, characterised in that the protuberance defines a thickening of material between the internal surface and the external surface; the thickening of material being located downstream of the cavity.

7. The device of claim 6, characterised in that the illuminator is entirely contained internally of the cavity for training the light beam against the thickening of material.

8. The device of claim 2, characterised in that the illuminator is entirely contained internally of the cavity for training the light beam against the closed front side of the cavity, the light beam being directed between the first internal surface and the second external surface of the retractor body.

9. The device of claim 1, characterised in that the laterally-developing walls and the closed front side of the cavity are entirely contained between an internal surface and an external surface of the retractor body.

10. The device of claim 1, characterised in that the handle comprises a first element, solidly constrained to the retractor body, and a second element, couplable to the first element.

11. The device of claim 1, characterised in that the handle comprises a first element, solidly constrained to the retractor body, and a second element, couplable to the first element, and wherein the second element exhibits a termination destined to fit in the cavity.

12. The device of claim 11, characterised in that the termination comprises a first seating for housing and retaining the illuminator.

13. A medical-surgical device for colo-proctological pathologies, comprising
    a one-piece retractor body which has been integrally provided as a single piece, the retractor body (a) having a direction of development along a prevalent axis, (b) having a distal end insertable in an anal cavity, and (c) having a proximal end, the retractor body having a side wall connecting the distal end to the proximal end;
    a handle, connected to the retractor body adjacent the proximal end for facilitating manoeuverability of the retractor body internally of the anal cavity;
    an illuminator for generating a light beam directed from the proximal end towards the distal end;
wherein the one-piece retractor body comprises a cavity afforded internally thereof in the side wall, the cavity extending from the proximal end of the one-piece retractor body towards the distal end of the one-piece retractor body, and wherein the illuminator is entirely contained internally of the cavity for generating the light beam directly internally of the retractor body, the cavity being enclosed by a top, laterally-developing walls and a bottom, the top and laterally-developing walls defining a protuberance which extends upwardly with respect to the retractor body side wall portions adjacent the protuberance.

\* \* \* \* \*